United States Patent
Boesen

(10) Patent No.: US 10,201,309 B2
(45) Date of Patent: Feb. 12, 2019

(54) DETECTION OF PHYSIOLOGICAL DATA USING RADAR/LIDAR OF WIRELESS EARPIECES

(71) Applicant: BRAGI GmbH, Müchen (DE)

(72) Inventor: Peter Vincent Boesen, München (DE)

( * ) Notice: Subject to any disclaimer, the term of this patent is extended or adjusted under 35 U.S.C. 154(b) by 0 days.

(21) Appl. No.: 15/347,698

(22) Filed: Nov. 9, 2016

(65) Prior Publication Data
US 2018/0014113 A1 Jan. 11, 2018

Related U.S. Application Data

(60) Provisional application No. 62/358,764, filed on Jul. 6, 2016.

(51) Int. Cl.
| | |
|---|---|
| A61B 5/00 | (2006.01) |
| H04R 1/10 | (2006.01) |
| G08B 3/10 | (2006.01) |
| G08B 5/36 | (2006.01) |
| G08B 21/04 | (2006.01) |
| G08B 25/10 | (2006.01) |
| A61F 5/00 | (2006.01) |

(52) U.S. Cl.
CPC .......... *A61B 5/6803* (2013.01); *A61B 5/0015* (2013.01); *A61B 5/0095* (2013.01); *G08B 3/10* (2013.01); *G08B 5/36* (2013.01); *G08B 21/0453* (2013.01); *G08B 25/10* (2013.01); *H04R 1/1016* (2013.01); *H04R 1/1091* (2013.01); *A61F 5/0013* (2013.01); *H04R 2420/07* (2013.01)

(58) Field of Classification Search
CPC combination set(s) only.
See application file for complete search history.

(56) References Cited

U.S. PATENT DOCUMENTS

| | | | |
|---|---|---|---|
| 2,325,590 | A | 8/1943 | Carlisle et al. |
| 2,430,229 | A | 11/1947 | Kelsey |
| 3,047,089 | A | 7/1962 | Zwislocki |
| D208,784 | S | 10/1967 | Sanzone |
| 3,586,794 | A | 6/1971 | Michaelis |
| 3,934,100 | A | 1/1976 | Harada |
| 3,983,336 | A | 9/1976 | Malek et al. |
| 4,069,400 | A | 1/1978 | Johanson et al. |

(Continued)

FOREIGN PATENT DOCUMENTS

| | | |
|---|---|---|
| CN | 204244472 U | 4/2015 |
| CN | 104683519 A | 6/2015 |

(Continued)

OTHER PUBLICATIONS

Announcing the $3,333,333 Stretch Goal (Feb. 24, 2014).

(Continued)

*Primary Examiner* — Amir Etesam
(74) *Attorney, Agent, or Firm* — Goodhue, Coleman & Owens, P.C.

(57) ABSTRACT

A system, method, and wireless earpieces for determining the status of the user. Sensor measurements of the user are performed utilizing a radar sensor of the wireless earpieces. The sensor measurements are analyzed. The status of the user is determined utilizing at least the sensor measurements of the radar sensor of the wireless earpieces. An alert is communicated to the user in response to there being a change in the status of the user.

7 Claims, 7 Drawing Sheets

(56) References Cited

U.S. PATENT DOCUMENTS

| | | |
|---|---|---|
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| D601,134 S | 9/2009 | Elabidi et al. |
| 7,825,626 B2 | 11/2010 | Kozisek |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| D666,581 S | 9/2012 | Perez |
| 8,300,864 B2 | 10/2012 | Müllenborn et al. |
| 8,406,448 B2 | 3/2013 | Lin |
| 8,436,780 B2 | 5/2013 | Schantz et al. |
| D687,021 S | 7/2013 | Yuen |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,229,227 B2 * | 1/2016 | Border ............... G02B 27/0093 |
| 9,461,403 B2 | 10/2016 | Gao et al. |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg et al. |
| D788,079 S | 5/2017 | Son et al. |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0074671 A1 | 4/2006 | Farmaner et al. |

(56) References Cited

U.S. PATENT DOCUMENTS

| | | |
|---|---|---|
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2008/0076972 A1 | 3/2008 | Dorogusker et al. |
| 2008/0090622 A1 | 4/2008 | Kim et al. |
| 2008/0146890 A1 | 6/2008 | LeBoeuf et al. |
| 2008/0254780 A1 | 10/2008 | Kuhl et al. |
| 2008/0255430 A1 | 10/2008 | Alexandersson et al. |
| 2009/0003620 A1 | 1/2009 | McKillop et al. |
| 2009/0017881 A1 | 1/2009 | Madrigal |
| 2009/0073070 A1 | 3/2009 | Rofougaran |
| 2009/0097689 A1 | 4/2009 | Prest et al. |
| 2009/0105548 A1 | 4/2009 | Bart |
| 2009/0191920 A1 | 7/2009 | Regen et al. |
| 2009/0245559 A1 | 10/2009 | Boltyenkov et al. |
| 2009/0296968 A1 | 12/2009 | Wu et al. |
| 2009/0299215 A1* | 12/2009 | Zhang .................... H04R 25/30 600/559 |
| 2010/0033313 A1 | 2/2010 | Keady et al. |
| 2010/0203831 A1 | 8/2010 | Muth |
| 2010/0210212 A1 | 8/2010 | Sato |
| 2010/0239126 A1* | 9/2010 | Grafenberg .......... A61B 5/1076 382/106 |
| 2010/0320961 A1 | 12/2010 | Castillo et al. |
| 2011/0137141 A1* | 6/2011 | Razoumov ........... A61B 5/0002 600/316 |
| 2011/0286615 A1 | 11/2011 | Olodort et al. |
| 2012/0057740 A1 | 3/2012 | Rosal |
| 2012/0197737 A1 | 8/2012 | LeBoeuf et al. |
| 2012/0235883 A1* | 9/2012 | Border ............... G02B 27/0093 345/8 |
| 2013/0237754 A1* | 9/2013 | Berglund ............... A61B 1/227 600/109 |
| 2013/0316642 A1 | 11/2013 | Newham |
| 2013/0346168 A1 | 12/2013 | Zhou et al. |
| 2014/0072146 A1 | 3/2014 | Itkin et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0163771 A1 | 6/2014 | Demeniuk |
| 2014/0185828 A1 | 7/2014 | Helbling |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0348367 A1 | 11/2014 | Vavrus et al. |
| 2015/0028996 A1 | 1/2015 | Agrafioti et al. |
| 2015/0110587 A1 | 4/2015 | Hori |
| 2015/0148989 A1 | 5/2015 | Cooper et al. |
| 2015/0245127 A1 | 8/2015 | Shaffer |
| 2016/0033280 A1 | 2/2016 | Moore et al. |
| 2016/0072558 A1 | 3/2016 | Hirsch et al. |
| 2016/0073189 A1 | 3/2016 | Lindén et al. |
| 2016/0125892 A1 | 5/2016 | Bowen et al. |
| 2016/0360350 A1 | 12/2016 | Watson et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0078780 A1 | 3/2017 | Qian et al. |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0257698 A1 | 9/2017 | Boesen et al. |
| 2017/0258329 A1* | 9/2017 | Marsh .................. A61B 5/0024 |

FOREIGN PATENT DOCUMENTS

| | | |
|---|---|---|
| CN | 104837094 A | 8/2015 |
| EP | 1017252 A2 | 7/2000 |
| EP | 1469659 A1 | 10/2004 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014043179 A2 | 3/2014 |
| WO | 2014046602 A1 | 3/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |

OTHER PUBLICATIONS

BRAGI Is on Facebook (2014).

BRAGI Update—Arrival of Prototype Chassis Parts—More People—Awesomeness (May 13, 2014).

BRAGI Update—Chinese New Year, Design Verification, Charging Case, More People, Timeline(Mar. 6, 2015).

BRAGI Update—First Sleeves From Prototype Tool—Software Development Kit (Jun. 5, 2014).

BRAGI Update—Let's Get Ready to Rumble, A Lot to Be Done Over Christmas (Dec. 22, 2014).

BRAGI Update—Memories From April—Update on Progress (Sep. 16, 2014).

BRAGI Update—Memories from May—Update on Progress—Sweet (Oct. 13, 2014).

BRAGI Update—Memories From One Month Before Kickstarter—Update on Progress (Jul. 10, 2014).

BRAGI Update—Memories From the First Month of Kickstarter—Update on Progress (Aug. 1, 2014).

BRAGI Update—Memories From the Second Month of Kickstarter—Update on Progress (Aug. 22, 2014).

BRAGI Update—New People @BRAGI—Prototypes (Jun. 26, 2014).

BRAGI Update—Office Tour, Tour to China, Tour to CES (Dec. 11, 2014).

(56) References Cited

OTHER PUBLICATIONS

BRAGI Update—Status on Wireless, Bits and Pieces, Testing6—Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, On Track(May 16, 2015).
BRAGI Update—Beta2 Production and Factory Line(Aug. 20, 2015).
BRAGI Update—Certifications, Production, Ramping Up.
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, On Track and Gems Overview.
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Last Push Before the Kickstarter Campaign Ends on Monday 4pm CET (Mar. 28, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
Weisiger, "Conjugated Hyperbilirubinemia", (Nov. 10, 2014).
Akkermans, "Acoustic Ear Recognition for Person Identification", Automatic Identification Advanced Technologies, 2005 pp. 219-223.
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
Healthcare Risk Management Review, "Nuance updates computer-assisted physician documentation solution" (Oct. 20, 2016).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces a Health + Mobility Concept for Wellness in Mobility", Fountain Valley, Califorma (2017).
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Weisiger; "Conjugated Hyperbilirubinemia", Jan. 5, 2016.

* cited by examiner

DETECTION OF PHYSIOLOGICAL DATA USING RADAR/LIDAR OF WIRELESS EARPIECES

PRIORITY STATEMENT

This application claims priority to U.S. Provisional Patent Application No. 62/358,764, filed Jul. 6, 2016, and entitled "DETECTION OF METABOLIC DISORDERS USING WIRELESS EARPIECES", hereby incorporated by reference in its entirety.

BACKGROUND

I. Field of the Disclosure

The illustrative embodiments relate to wireless earpieces. More specifically, but not exclusively, the illustrative embodiments relate to wireless earpieces for and monitoring user biometrics and input including through the use of radar and/or lidar.

II. Description of the Art

The growth of wearable devices is increasing exponentially. This growth is fostered by the decreasing size of microprocessors, circuity boards, chips, and other components. In some cases, wearable devices may obtain biometric data. An important aspect of biometric data is monitoring metabolic abnormalities. In some cases, detecting metabolic abnormalities may be difficult because of the small changes over time, location, user activity, and access to equipment or devices that may be configured to detect such conditions.

SUMMARY OF THE DISCLOSURE

One embodiment of the illustrative embodiments provides a system, method, and wireless earpieces for determining the status of the user. Sensor measurements of the user are performed utilizing at least a radar sensor of the wireless earpieces. The sensor measurements are analyzed. The status of the user is determined utilizing at least the sensor measurements of the radar sensor of the wireless earpieces. An alert is communicated to the user in response to there being a change in the status of the user. Another embodiment provides wireless earpieces including a processor and a memory storing a set of instructions. The set of instructions are executed to perform the method described.

Another embodiment provides a wireless earpiece. The wireless earpiece may include a frame for fitting in an ear of a user. The wireless earpiece may also include a logic engine controlling functionality of the wireless earpiece. The wireless earpiece may also a number of sensors measuring biometric readings of the user. The sensors may include at least a radar sensor. The wireless earpiece may also include a transceiver communicating with at least a wireless device. The logic engine analyzes the biometric readings, determines a status of the user utilizing the biometric readings from the radar sensor, and communicates an alert to the user in response to there being a change in the status of the user.

BRIEF DESCRIPTION OF THE DRAWINGS

Illustrated embodiments of the present invention are described in detail below with reference to the attached drawing figures, which are incorporated by reference herein, and where.

DETAILED DESCRIPTION OF THE DISCLOSURE

Figure 1:
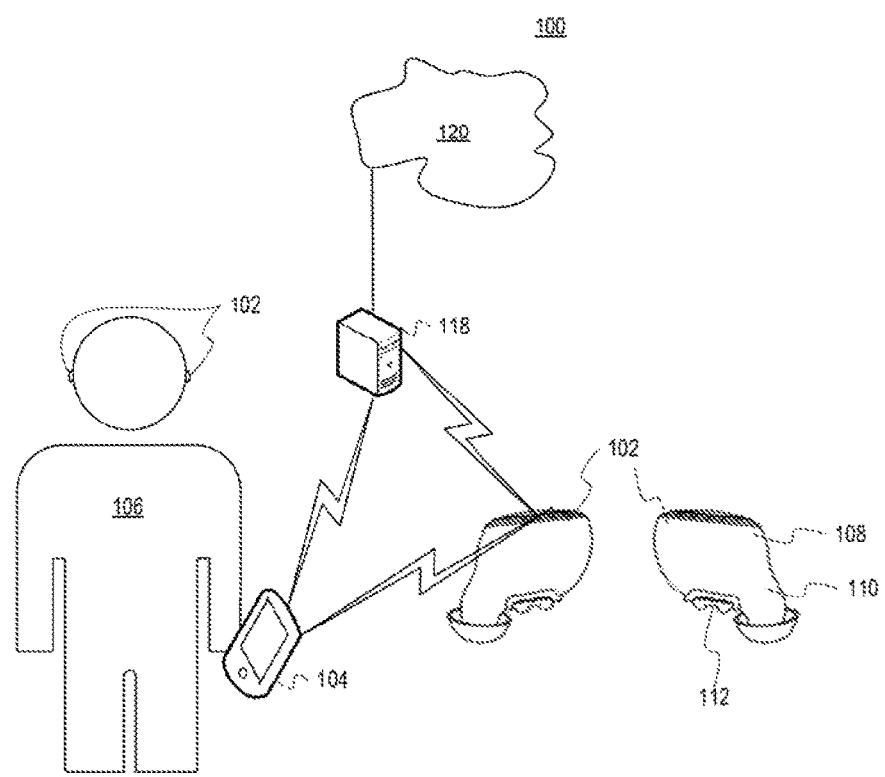
FIG. 1 is a pictorial representation of a communication system in accordance with an illustrative embodiment.

The illustrative embodiments provide a system, method, wireless earpieces, and personal area network for determining user biometrics including metabolic disorders. The wireless earpieces may include any number of sensors for measuring blood oxygenation, chemical compounds present within or excreted by the user, blood pressure, respiration, temperature, pulse rate, and associated changes in the sensor measurements. In response to detecting a metabolic abnormality associated with one or more thresholds, an alert may be communicated to the user through the wireless earpieces or to the user or other designated parties through one or more additional computing or communications devices.

The wireless earpieces may also be utilized to control, communicate, manage or interact with a number of other wearable devices, such as smart glasses, helmets, smart glass, watches or wrist bands, chest straps, implants, displays, clothing, or so forth, In one embodiment, the wireless earpieces may be part of a personal area network. A personal area network is a network tar data transmissions among devices, such as personal computing, communications, camera, vehicles, entertainment, and medical devices. The personal area network may utilize any number of wired, wireless, or hybrid configurations and may be stationary or dynamic. For example, the personal area network may utilize wireless network protocols or standards, such as INSTEON, IrDA, Wireless USB near field magnetic induction (NFMI), Bluetooth, Z-Wave, ZigBee, ANT+ or other applicable radio frequency signals. In one embodiment, the personal area network may move with the user.

The wireless earpieces may include my number of sensors for reading user biometrics, such as pulse rate, blood pressure, blood oxygenation, temperature, calories expended, blood or sweat chemical content, voice and audio output, impact levels, and orientation (e.g., body, head, etc.). The sensors may also determine the user's location, position, velocity, impact levels, and so forth. The sensors may also receive user input and convert the user input into commands or selections made across the personal devices of the personal area network. For example, the user input detected by the wireless earpieces may include voice commands, head motions, finger taps, finger swipes, motions or gestures, or other user inputs sensed by the wireless earpieces. The user input may be determined and converted into commands that may be sent to one or more external devices, such as a tablet computer, smart phone, or so forth.

The wireless earpieces may perform sensor measurements for the user to read any number of user biometrics. The user biometrics may be analyzed including measuring deviations or changes of the sensor measurements over time, identifying trends of the sensor measurements, and comparing the sensor measurements to control data for the user. As the sensor measurements are analyzed, analysis is performed to determine whether they exceed one or more thresholds. The thresholds may be set by default, the user, an administrator, a caregiver, or other parties. The thresholds may include a high threshold and a low threshold (e.g., temperature, blood pressure, heart rate, etc.) that may be utilized to determine whether an event is automatically triggered by the wireless earpieces. The event may include a communication to the user including a warning that a threshold has been exceeded. The warning may also specify the user's biometrics or sensor readings that triggered the event as well as the thresholds themselves so that the user may be alerted. The warning may include information, such as trends in sensor measurements, potential condition of the user, and other applicable information.

In one embodiment, the sensors of the wireless earpieces may detect metabolic abnormalities, a critical factor in providing appropriate diagnosis and treatment to users. In some cases, metabolic abnormalities progress slowly without causing appreciable discomfort or distress on the part of the patient. In other cases, the onset of metabolic abnormalities may be quite rapid and the consequences of non-diagnosis or delayed diagnosis may lead to significant issues with morbidity or even mortality. One such example of a need for rapid diagnosis of a disease state involves diabetic ketoacidosis. Diabetic ketoacidosis may be characterized by the development of high concentrations of ketone bodies in the bloodstream. Ketones are the byproducts of the breakdown of fatty-acids by the body. Ketones may rapidly accumulate in the bloodstream with the most common types being beta-hydroxybutyrate and acetoacetic acid. The metabolic state of ketoacidosis may be caused by the body's inability to adequately regulate ketone production which may lead to acidification of the blood pH and metabolic acidosis. The various types of metabolic abnormalities may present a serious threat to the well-being of the patient. For example, rapid diagnosis of ketoacidosis is essential to successful intervention thereby minimizing increased risks of morbidity and mortality.

In one embodiment, ketones may be detected in the sweat or excretions of the user as detected by the sensors of the wireless earpieces. Other metabolic disorders may cause pigmentary changes in the skin. One such example is hyperbilirubinemia. Billy Rubin may accumulate in the blood stream due to the breakdown of red blood cells. When red blood cells break down, bilirubin (a tetrapyrrole) is produced through the breakdown of hemoproteins such as hemoglobin. If the bilirubin level is too high, deposition of the yellow colored bilirubin pigments occur in multiple tissues, such as the skin, sclerae, and other tissues, such as the mucous membranes. These changes may cause an icteric appearance to the skin through a gradual yellowing pigmentation. It is imperative to identify the signs of icterus. The sensors may sense changes to the pigments of the skin associated with ketones.

The wireless earpieces may include any number of biometric sensors for monitoring and detecting metabolic states. For example, an optical sensor utilizing a blue LED may be useful for detecting yellow pigments associated with elevated levels of bilirubin. The blue LEDs (or other optical, spectroscopy sensors) may directly contact the epithelium of the external auditory canal or auricular regions. As a result, the bilirubin levels may be monitored in real-time without the need for blood draws to determine the status of the user.

The wireless earpieces may also detect ketones, such as the acidification of sweat that may be an indicator of the emergence of such a condition. The wireless earpieces may also include chemical sensors that may measure chemicals in the sweat and other excretions of the user. The wireless earpieces may also be configured to be blown on by the user to detect ketones in the breath of the user. The sensors for detecting metabolic disorders may work with the FIG. 1 is a pictorial representation of a communications environment 100 in accordance with an illustrative embodiment. The wireless earpieces 102 may be configured to communicate with each other and with one or more wireless devices, such as a wireless device 104 or a tracking device 118. The wireless earpieces 102 may be worn by a user 106 and are shown as worn and separately from their positioning within the ears of the user 106 for purposes of visualization. A block diagram of the wireless earpieces 102 if further shown in FIG. 2 to further illustrate components and operation of the wireless earpieces 102.

In one embodiment, the wireless earpieces 102 includes a frame 108 shaped to fit substantially within the ears of the user 106. The frame 108 is a support structure that at least partially encloses and houses the electronic components of the wireless earpieces 102. The frame 108 may be composed of a single structure or multiple structures that are interconnected. The frame 108 defines an extension 110 configured to fit substantially within the ear of the user 106. The extension 110 may include one or more speakers or vibration components for interacting with the user 106. The extension 110 may be removable covered by one or more sleeves. The sleeves may be changed to fit the size and shape of the user's ears. The sleeves may come in various sizes and have extremely tight tolerances to fit the user 106 and one or more other users that may utilize the wireless earpieces 102 during their expected lifecycle. In another embodiment, the sleeves may be custom built to support the interference fit utilized by the wireless earpieces 102 while also being comfortable while worn. The sleeves are shaped and configured to not cover various sensor devices of the wireless earpieces 102.

In one embodiment, the frame 108 or the extension 110 (or other portions of the wireless earpieces 102) may include sensors 112 for sensing pulse, blood oxygenation, temperature, voice characteristics, skin conduction, glucose levels, impacts, activity level, position, location, orientation, as well as any number of internal or external user biometrics. In other embodiments, the sensors 112 may be internally positioned within the wireless earpieces 102. For example, the sensors 112 may represent metallic contacts, optical interfaces, or micro-delivery systems for receiving and delivering information. Small electrical charges may be passed through the sensors 112 to analyze the biometrics of the user 106 including pulse, skin conductivity, blood analysis, sweat levels, and so forth. Sensors 112 may also be utilized to sense or provide a small electrical current which may be useful for alerting the user, stimulating blood flow, alleviating nausea, or so forth.

In some applications, temporary adhesives or securing mechanisms (e.g., clamps, straps, lanyards, extenders, etc.) may be utilized to ensure that the wireless earpieces 102 remain in the ears of the user 106 even during the most rigorous and physical activities or that if they do fall out they are not lost or broken. For example, the wireless earpieces 102 may be utilized during marathons, swimming, team sports, biking, hiking, parachuting, or so forth. The wireless earpieces 102 may be configured to play music or audio, receive and make phone calls or other communications, determine ambient environmental conditions (e.g., temperature, altitude, location, speed, heading, etc.), read user biometrics (e.g., heart rate, motion, temperature, sleep, blood oxygenation, voice output, calories burned, forces experienced, etc.), and receive user input, feedback, or instructions. The wireless earpieces 102 may be utilized with any number of automatic assistants, such as Siri, Cortana, or other smart assistant.

The communications environment 100 may further include a tracking device 118. The tracking device 118 may communicate with one or more wired or wireless networks, such as a network 120, The tracking device 118 may represent any number of devices, systems, equipment, or components, such as a point of personal computer, server, tablet, medical system, or so forth. The tracking device 118 may communicate utilize any number of standards, protocols, or processes. For example, the tracking device 118 may utilize a wired or wireless connection to communicate with the wireless earpieces 102, the wireless device 104, or other electronic devices. The tracing device 118 may utilize any number of memories or databases to store biometric information associated with the user 106 including The wireless earpieces 102 may determine their position with respect to each other as well as the wireless device 104 and the tracking device 118. For example, position information for the wireless earpieces 102 and the wireless device 104 may determine proximity of the devices in the communications environment 100. For example, global positioning information or signal strength/activity may be utilized to determine proximity and distance of the devices to each other in the communications environment 100. In one embodiment, the distance information may be utilized to determine whether biometric analysis may be displayed to a user. For example, the wireless earpieces 102 may be required to be within four feet of the wireless device 104 and the tracking device 118 in order to display biometric readings or receive user input.

In one embodiment, the wireless earpieces 102 and the corresponding sensors 112 (whether internal or external) may be configured to take a number of measurements or log information during normal usage. The sensor measurements may be utilized to extrapolate other measurements, factors, or conditions applicable to the user 106. For example, the sensors 112 may monitor the user's ketone levels to determine real-time metabolic conditions as well as to monitor the daily, weekly, or yearly patterns and characteristics to determine the user's status. The user 106 or another party may configure the wireless earpieces 102 directly or through a connected device and app (e.g., mobile app with a graphical user interface) to store or share biometric information, audio, readings, and other data. Some examples of standard usage may include detecting and recording a heartbeat, tracking ketone levels per time period (e.g., minutes, hours, etc.) or based on certain events or thresholds.

The user 106 or another party may also utilize the wireless device 104 to associate biometric information and conditions with the actual or perceived status of the user 106. For example, ketone or hyperbilitubinemia levels may be associated with the condition of the user 106 as determined by a medical professional or as characterized by the user. As a result, the wireless earpieces 102 may be adjusted or trained over time to become even more accurate in reading biometric information of the user 106. The wireless earpieces 102 may utilize historical information to generate default values, baselines, thresholds, policies, or settings for determining when and how the user's biometric identifiers are read. As a result, the wireless earpieces may more accurately diagnose the metabolic status of the user 106.

The wireless earpieces 102 may include any number of sensors 112 and logic for measuring and determining user biometrics, such as pulse rate, skin conduction, blood oxygenation, temperature, calories expended, blood or excretion chemistry, voice and audio output, position, and orientation (e.g., body, head, etc.). The sensors 112 may also determine the user's location, position, velocity, impact levels, and so forth. The sensors 112 may also receive user input and convert the user input into commands or selections made across the personal devices of the personal area network. For example, the user input detected by the wireless earpieces 102 may include voice commands, head motions, finger taps, linger swipes, motions or gestures, or other user inputs sensed by the wireless earpieces. The user input may be determined by the wireless earpieces 102 and converted into authorization commands that may be sent to one or more external devices, such as the wireless device 104, the tracking device 118, a tablet computer, or so forth. For example, the user 106 may create a specific head motion and voice command that when detected by the wireless earpieces 102 are utilized to initiate biometric readings, such as checking the status of the user 106. The wireless earpieces 102 may perform any number of non-invasive or invasive processes or procedures (e.g., taking a blood sample to measure chemical compositions).

The sensors 112 may make all of the measurements with regard to the user 106 or may communicate with any number of other sensory devices in the communications environment 100 to measure information and data about the user 106 as well as the communications environment 100 itself. In one embodiment, the communications environment 100 may represent all or a portion of a personal area network. The wireless earpieces 102 may be utilized to control, communicate, manage, or interact with a number of other wearable devices or electronics, such as smart glasses, helmets, smart glass, watches or wrist bands, other wireless earpieces, chest straps, implants, displays, clothing, or so forth. A personal area network is a network for data transmissions among devices, such as personal computing, communications, camera, vehicles, entertainment, and medical devices. The personal area network may utilize any number of wired, wireless, or hybrid configurations and may be stationary or dynamic. For example, the personal area network may utilize wireless network protocols or standards, such as INSTEON, IrDA, Wireless USB, Bluetooth, Z-Wave, ZigBee, Wi-Fi, ANT+ or other applicable radio frequency signals. In one embodiment, the personal area network may move with the user 106.

In other embodiments, the communications environment 100 may include any number of devices, components, or so forth that may communicate with each other directly or indirectly through a wireless (or wired) connection, signal, or link. The communications environment 100 may include one or more networks and network components and devices represented by the network 120, such as routers, servers, signal extenders, intelligent network devices, computing devices, or so forth, in one embodiment, the network 120 of the communications environment 100 represents a personal area network as previously disclosed. The network 120 may also be a health network including devices and processes for simultaneously monitoring the health of a number of users.

Communications within the communications environment 100 may occur through the network 120 or a Wi-Fi network or may occur directly between devices, such as the wireless earpieces 102 and the wireless device 104. The network 120 may communicate with or include a wireless network, such as a Wi-Fi, cellular (e.g., 3G, 4G, 5G, PCS, GSM, etc.), Bluetooth, or other short range or long range radio frequency networks. The network 120 may also include or communicate with any number of hard wired networks, such as local area networks, coaxial networks, fiber-optic networks, network adapters, or so forth. Communications within the communications environment 100 may be operated by one or more users, service providers, or network providers.

The wireless earpieces 102 may play, communicate, or utilize any number of alerts or communications to indicate that the status of the user. For example, one or more alerts may indicate when health and metabolic tracking is pending, in process, authorized, and/or alerted with specific tones, verbal acknowledgements, tactile feedback, or other forms of communicated messages. For example, an alert may be played during each stage of the tracking. The corresponding alert may also be communicated to the user 106, the wireless device 104, and the tracking device 118.

In other embodiments, the wireless earpieces 102 may also vibrate, flash, play a tone or other sound, or give other indications of the health status of the user in order to prompt user actions (e.g., providing additional biometric readings, eat or drink, go to the Doctor, etc.) or implement any number of processes. The wireless earpieces 102 may also communicate an alert to the wireless device 104 that shows up as a notification, message, or other indicator indicating the changed status of the tracking.

The wireless earpieces 102 as well as the wireless device 104 may include logic far automatically implementing actions in response to a pending tracking or various conditions and factors of the communications environment 100. For example, the wireless device 104 may communicate instructions received from the wireless earpieces 102 for the user 106 to visit the nurse at school to be checked on. The wireless device 104 may include an application that displays instructions and information to the user 106 in response to the determined status of the user.

In one embodiment, the wireless device 104 may utilize short-range or long-range wireless communications to communicate with the wireless earpieces 102 through a wireless signal or devices of the communications environment 100. For example, the wireless device 104 may include a Bluetooth and cellular transceiver within the embedded logical components. For example, the wireless signal may be a Bluetooth, Wi-Fi, Zigbee, Ant+, near-field magnetic induction (NFMI), or other short range wireless communication.

The wireless device 104 may represent any number of wireless or wired electronic communications or computing devices, such as smart phones, laptops, desktop computers, control systems, tablets, displays, gaming devices, music players, personal digital assistants, vehicle systems, or so forth. The wireless device 104 may communicate utilizing any number of wireless connections, standards, or protocols (e.g., near field communications, NFMI, Bluetooth, Wi-Fi, wireless Ethernet, etc.). For example, the wireless device 104 may be a touch screen cellular phone that communicates with the wireless earpieces 102 utilizing Bluetooth communications. The wireless device 104 may implement and utilize any number of operating systems, kernels, instructions, or applications that may make use of the available sensor data sent from the wireless earpieces 102. For example, the wireless device 104 may represent any number of android, iOS, Windows, open platforms, or other systems and devices. Similarly, the wireless device 104 or the wireless earpieces 102 may execute any number of applications that utilize the user input, proximity data, biometric data, and other feedback from the wireless earpieces 102 to initiate, authorize, or process health tracking and perform the associated tasks.

As noted, the layout of the internal components of the wireless earpieces 102 and the limited space available for a product of limited size may affect where the sensors 112 may be positioned. The positions of the sensors 112 within each of the wireless earpieces 102 may vary based on the model, version, and iteration of the wireless earpiece design and manufacturing process and the particular type of sensors. Different sensors may be located in different positions based on their functionality. The sensor location designated in FIG. 1 provides for contact with skin of a user and thus is particularly well-suited for physiological sensing, although such sensors may otherwise be located or positioned.

Figure 2:
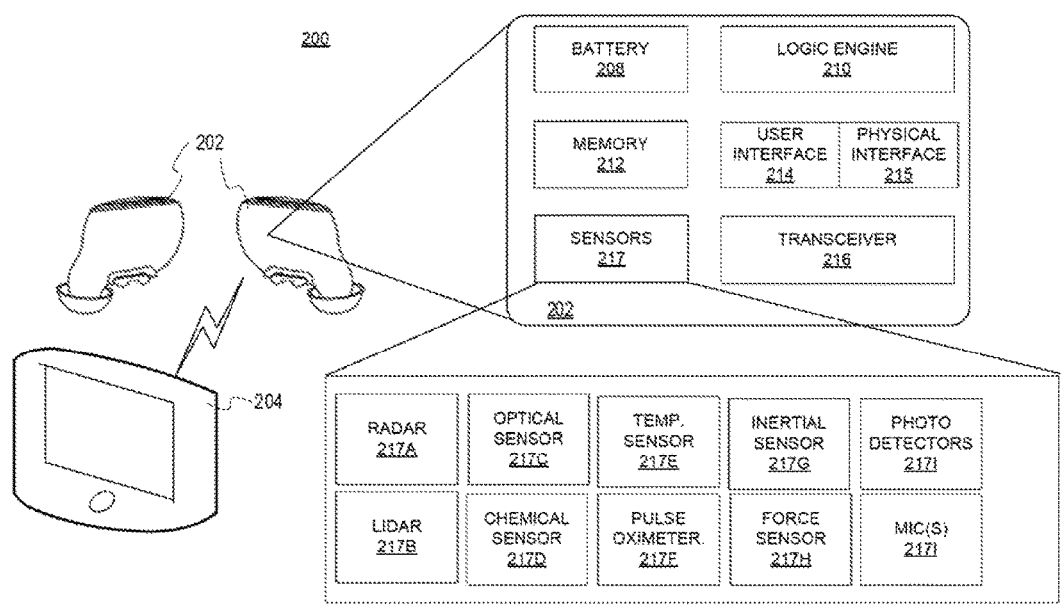
FIG. 2 is a block diagram of wireless earpieces in accordance with an illustrative embodiment.

FIG. 2 further illustrates a block diagram of the wireless earpieces 202. As noted, the components of the wireless earpieces 202 may be described collectively rather than individually. The wireless earpieces 202 may be wirelessly linked to any number of wireless devices, such as the wireless device 104 of FIG. 1. For example, wireless devices may include wearable devices, communications devices, computers, entertainment devices, vehicle systems, exercise equipment, or so forth. Sensor measurements, user input, and commands may be received from either the wireless earpieces 202 or the wireless device (not shown) for processing and implementation on either of the devices (or other externally connected devices). Reference to the wireless earpieces 202 may descriptively or functionally refer to either the pair of wireless earpieces (wireless earpieces) or individual wireless earpieces (left wireless earpiece and right wireless earpiece) without limitation.

In some embodiments, the wireless device may also act as a logging tool for sensor data or measurements made by the wireless earpieces 202. For example, the wireless device may receive and share data captured by the wireless earpieces 202 in real-time including biometric information, such as a tracking biometrics or input or status of the user (e.g., physical, emotional, etc.). As a result, the wireless device may be utilized to store, display, and synchronize sensor data received from the wireless earpieces 202. For example, the wireless device may display user pulse rate, temperature, ketone levels, proximity, location, blood oxygenation, distance, calories burned, and so forth as measured by the wireless earpieces 202. The wireless device may be configured to receive and display alerts that indicate conditions to initiate, process, and track a user's condition or specific symptoms. For example, if a metabolic state is detected based on ketones thresholds, the wireless earpieces 202 may automatically display an alert, message, in-app communication, such as "please verify your metabolic condition, you may need medical treatment based on your detected ketone levels." The wireless earpieces 202 and the wireless device may have any number of electrical configurations, shapes, and colors and may include various circuitry, connections, and other components utilized to perform the illustrative embodiments.

In one embodiment, the wireless earpieces 202 may include a battery 208, a logic engine 210, a memory 212, a user interface 214, a physical interface 215, a transceiver 216, and sensors 217. The wireless earpieces 202 and the wireless device 202 may have any number of configurations and include components and features as are known in the art. In one embodiment, the wireless earpieces 202 may include a module specifically for performing noise cancellation. For example, determinations of noise cancelling signals may be determined in one wireless earpiece and health biometrics may be monitored in the other wireless earpiece, with coordination of determinations, actions, and so forth synchronized between both wireless earpieces 202.

The battery 208 is a power storage device configured to power the wireless earpieces 202. In other embodiments, the battery 208 may represent a fuel cell, thermal electric generator, piezo electric charger, solar charger, ultra-capacitor, or other existing or developing power storage technologies. The sensors 217 may also be utilized to measure the temperature of the battery 208 and the condition of internal components of the wireless earpieces. The sensors may also be utilized to determine data about external conditions and factors applicable to the user, the user's environment, a communicating wireless device, or so forth. Other conditions and factors sensed by the sensors 217 (e.g., water/humidity, pressure, ketone levels, blood oxygenation, blood content levels, altitude, position, impact, radiation, etc.) may also be determined with the data being processed by the logic engine 210.

The logic engine 210 is the logic that controls the operation and functionality of the wireless earpieces 202. The logic engine 210 may include circuitry, chips, and other digital logic. The logic engine 210 may also include programs, scripts, and instructions that may be implemented to operate the logic engine 210. The logic engine 210 may represent hardware, software, firmware, or any combination thereof. In one embodiment, the logic engine 210 may include one or more processors. The logic engine 210 may also represent an application specific integrated circuit (ASIC) or field programmable gate array (FPGA). The logic engine 210 may utilize sensor measurements, user input, user preferences and settings, conditions, factors, and environmental conditions to determine the identity of the user, at least in part, from measurements performed by the wireless earpieces 202.

The wireless earpieces 202 may function separately or together to authenticate biometric tracking is allowed by an authorized user. For example, processing may be divided between the wireless earpieces 202 to increase the speed of processing and to load balance any processes being performed. For example, a left wireless earpiece may perform imaging of the user's ear to identify the user while the right wireless earpiece may measure biometrics and identify voice characteristics of the wireless earpieces. Multiple forms of identifying information may be utilized to better secure information authenticated through the wireless earpieces.

In one embodiment, the logic engine 210 may determine the metabolic condition based on measurements and data from the sensors 217. The logic engine 210 may also perform any number of mathematical functions (e.g. linear extrapolation, polynomial extrapolation, conic extrapolation, French curve extrapolation, polynomial interpretation) to determine or infer the user biometrics, condition, identity, or other information of the user associated with the sensor measurements. The logic engine 210 may utilize time and other sensor measurements as causal forces to enhance a mathematical function utilized to perform the determinations, processing, and extrapolation performed by the logic engine 210. The logic engine 210 may also utilize historical information from the user/other users to better determine the state, condition, and other information associated with the user. Mathematical analysis of the user's overall physiological status may be determined from pulse rate, pulse rate variability, oxygen saturation, temperature, respiratory rate, systolic and diastolic blood pressure, and so forth.

The logic engine 210 may also process user input to determine biometric-related commands implemented by the wireless earpieces 202 or sent to the wireless earpieces 202 through the transceiver 216. Specific actions may be allowed, initiated, or implemented based on sensor measurements, extrapolated measurements, environmental conditions, proximity thresholds, and so forth. For example, the logic engine 210 may implement a biometric tracking macro performing a specific battery of tests each morning to determine the user's ketone levels, metabolic state, and overall health status. Various tests and different types of status checks may be performed utilizing a pre-defined schedule. The pre-defined schedule may be set by the user, an administrator of the wireless earpieces, a medical professional, or other authorized party.

In one embodiment, a processor included in the logic engine 210 is circuitry or logic enabled to control execution of a set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks.

The memory 212 is a hardware element, device, or recording media configured to store data or instructions for subsequent retrieval or access at a later time. The memory 212 may represent static or dynamic memory. The memory 212 may include a hard disk, random access memory, cache, removable media drive, mass storage, or configuration suitable as storage for data, instructions, and information. In one embodiment, the memory 212 and the logic engine 210 may be integrated. The memory may use any type of volatile or non-volatile storage techniques and mediums. The memory 212 may store information related to the user, wireless earpieces 202, wireless device 204, and other peripherals, such as a wireless device, smart glasses, smart watch, smart case for the wireless earpieces 202, wearable device, and so forth. In one embodiment, the memory 212 may display or communicate instructions, programs, drivers, or an operating system for controlling the user interface 214 including one or more LEDs or other light emitting components, speakers, tactile generators (e.g., vibrator), and so forth. The memory 212 may also store biometric readings, user input required for specified tracking processes, biometric tracking settings and preferences, thresholds, conditions, signal or processing activity, historical information, proximity data, and so forth.

The transceiver 216 is a component comprising both a transmitter and receiver which may be combined and share common circuitry on a single housing. The transceiver 216 may communicate utilizing NFMI, Bluetooth, Wi-Fi, ZigBee, Ant+, near field communications, wireless USB, infrared, mobile body area networks, ultra-wideband communications, cellular (e.g., 3G, 4G, 5G, PCS, GSM, etc.), infrared, or other suitable radio frequency standards, networks, protocols, or communications. For example, the transceiver 216 may coordinate communications and actions between the wireless earpieces 202 utilizing NFMI communications. The transceiver 216 may also be a hybrid, dual, or multi-mode transceiver that supports a number of different communications simultaneously. For example, the transceiver 216 may communicate with wireless devices or other systems utilizing wired interfaces (e.g., wires, traces, etc.), NFC or Bluetooth communications. The transceiver 216 may also detect amplitudes and infer distance between the wireless earpieces 202 and external devices, such as the wireless device or a smart case of the wireless earpieces 202.

The components of the wireless earpieces 202 may be electrically connected utilizing any number of wires, contact points, leads, busses, wireless interfaces, or so forth. In addition, the wireless earpieces 202 may include any number of computing and communications components, devices or elements which may include busses, motherboards, circuits, chips, sensors, ports, interfaces, cards, converters, adapters, connections, transceivers, displays, antennas, and other similar components.

The physical interface 215 is hardware interface of the wireless earpieces 202 for connecting and communicating with wireless devices or other electrical components, devices, or systems, The physical interface 215 may include any number of pins, arms, or connectors for electrically interfacing with the contacts or other interface components of external devices or other charging or synchronization devices. For example, the physical interface 215 may be a micro USB port. In one embodiment, the physical interface 215 is a magnetic interface that automatically couples to contacts or an interface of a wireless device. In another embodiment, the physical interface 215 may include a wireless inductor for charging the wireless earpieces 202 without a physical connection to a charging device.

The user interface 214 is a hardware interface for receiving commands, instructions, or input through the touch (haptics) of the user, voice commands, or predefined motions. For example, the user interface 214 may include a touch screen, one or more cameras or image sensors, microphones, speakers, and so forth. The user interface 214 may be utilized to control the other functions of the wireless earpieces 202. The user interface 214 may include the LED array, one or more touch sensitive buttons or portions, a miniature screen or display, or other input/output components. The user interface 214 may be controlled by the user or based on commands received from the wireless device. For example, the user may turn on, reactivate, or provide feedback utilizing the user interface 214, such as an application executed by the logic engine 210 and displayed by a touch screen of the user interface 214 to display information and receive user selections and feedback.

In one embodiment, the user interface 214 may include a fingerprint scanner that may be utilized to scan a fingerprint (e.g., the index finger) of a user to authenticate biometric readings and reporting. The user interface 214 of each of the wireless earpieces 202 may store identifying information for one or more fingers. In one embodiment, the biometric data of the user may be encrypted and stored within a secure portion of the memory 212 to prevent unwanted access or hacking. The wireless earpieces 202 may also store additional important biometric data, such as medical information (e.g., medical conditions, allergies, logged biometrics, contacts, etc.) that may be shared regularly, in response to threshold conditions being met, or in response to an emergency. The wireless earpieces 202 may also include one or more external microphones for playing alerts or providing information to external parties.

In one embodiment, the user may provide user feedback for authenticating a biometric reading, specified action, or authorization by tapping the user interface 214 once, twice, three times, or any number of times. Similarly, a swiping motion may be utilized across or in front of the user interface 214 (e.g., the exterior surface of the wireless earpieces 202) to implement a predefined action. Swiping motions in any number of directions or gestures may be associated with specific actions as well as other activities, such as share exercise data, share music playlist, share vitals, play music, pause, fast forward, rewind, activate a digital assistant (e.g., Siri, Cortana, smart assistant, etc.), or so forth without limitation. The swiping motions may also be utilized to control actions and functionality of wireless devices or other external devices e.g., smart television, camera array, smart watch, etc.). The user may also provide user input for authenticating an action by moving his head in a particular direction or motion or based on the user's position or location. For example, the user may utilize voice commands, head gestures, or touch commands to change the content visually displayed by the wireless device 20 or audibly communicated by the wireless earpieces 202. The user interface 214 may also provide a software interface including any number of icons, soft buttons, windows, links, graphical display elements, and so forth.

In one embodiment, the user interface 214 may periodically utilize one or more microphones and speakers of the wireless earpieces to authenticate the user. The microphone of the user interface 214 may measure various voice characteristics including amplitude, shimmer rates (i.e., changes in amplitude over time) frequency/pitch, jitter rates (i.e., changes in frequency data over time), accent, voice speed, inflection, and so forth. The wireless earpieces 202 may also recognize a pre-defined vocabulary. For example, specific words may be required to authenticate different tracking types.

The sensors 217 may include pulse oximeters, accelerometers, gyroscopes, magnetometers, water, moisture, or humidity detectors, impact/force detectors, chemical sensors (e.g., analysis of sweat, blood, etc.), thermometers, inertial sensors, photo detectors, miniature cameras, microphones, and other similar instruments for detecting the user's status as well as location, utilization of the wireless earpieces 202, orientation, motion, and so forth. The sensors 217 may also be utilized to determine the biometric, activity, location, and speed measurements of the user. In one embodiment, the sensors 217 may store data that may be shared with other components (e.g., logic engine 210), users, and devices.

The sensors 217 may include photodetectors, ultrasonic mapping devices, lidar, or radar that scan the ear of the user when positioned for utilization. The sensors 217 may generate a two or three dimensional scan or topography map of the user's ear and surrounding areas when the wireless earpieces 202 are properly positioned. The mapping may include the internal and/or external portions of the user's ear. The topographical image of the user's ear may be utilized as a stand-alone biometric identifier or may be utilized with other biometric identifiers to identify the user. The image may include the external auditory meatus, scapha, fossa triangularis, scaphoid fossa, helix, antihelix, antitragus, lobule, the tragus, and pinna as well as other internal or external portions of the ear and surrounding head structure.

Where the sensors 17 include radar sensors 217A, the radar sensors 217A may be single chip radar sensors or may be integrated with other integrated circuits on the device. The radar sensor 217A may be used to provide for biometric monitoring through picking up movements including small, subtle, or micro-movements. One example of such a movement is movement of a tympanic membrane. The radar sensor 217A may be oriented towards the inner ear and may be used to detect movement of the tympanic membrane. The radar sensor 217A may be oriented towards the skin of the user and used to determine movements associated with pulse or heart rate. The radar sensor 217A may be otherwise oriented for other purposes such as directed outwardly to detect obstacles or possible collisions in advance.

Where the sensors 17 include lidar sensors 217B, the lidar sensors 217B may be single chip lidar sensors or may be integrated with other integrated circuits on the device. The lidar sensor 217B may be used to provide for biometric monitoring. For example, the lidar sensor 217B may be positioned to scan an inner portion of an ear of the user. Thus, the inner ear portion of a user may be mapped. This may be used in order to identify a user or to observe changes in ear structure over time including differences in cerumen amount or location. It may also aid a user by determining whether the earpiece is positioned correctly within the ear.

Other types of sensors include optical sensors 217C, chemical sensors 217D, temperature sensors 217E, pulse oximeters 217F, inertial sensors 217G which may include accelerometers, magnetometers, compasses, or other inertial sensors, force sensors 217H, photo detectors 217I, and microphones 217J which may include air conduction microphones and/or bone conduction microphones.

Externally connected wireless devices may include components similar in structure and functionality to those shown for the wireless earpieces 202. For example, the wireless device 204 may include any number of processors, batteries, memories, busses, motherboards, chips, transceivers, peripherals, sensors, displays, cards, ports, adapters, interconnects, sensors, and so forth. In one embodiment, the wireless device 204 may include one or more processors and memories for storing instructions. The instructions may be executed as part of an operating system, application, browser, or so forth to implement the features herein described. For example, the user may set preferences for the wireless earpieces 202 to work individually or jointly to identify user biometrics for comparison against known values to determine the user's status or identify variations or abnormalities that may be associated with specific conditions, sicknesses, diseases, identifiers, warnings, or other information. Likewise, the preferences may manage the actions taken by the wireless earpieces 202 in response to identifying specific users are utilizing the wireless earpieces 202. For example, a parent user may have full access to schedule any number of biometric readings for a child that utilizes the wireless earpieces 202 with the results reported directly to one or more of the parents. Results of the user's metabolic state may also be automatically sent to a medical professional for association with the user. The data may be analyzed in real-time or logged to provide a history of measurements for determining trends or statistical results.

The wireless device may also execute an application with settings or conditions for updating, synchronizing, sharing, saving, processing, and utilizing biometric information. For example, one of the sensors 217 that may have failed may be ignored in response to improper or unreliable data being gathered. As a result, the user identification process for tracking authorization may be dynamically performed utilizing any combination of sensor measurements, For example, the number and position of the sensors 217 utilized to perform status determinations for the user may vary based on failures, inaccurate data, or other temporary or permanent issues with hardware and software of the wireless earpieces 202.

Figure 3:
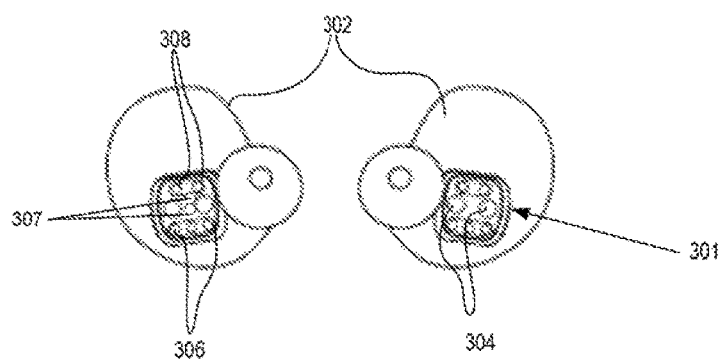
FIG. 3 is a pictorial representation of sensors of the wireless earpieces in accordance with illustrative embodiments.

FIG. 3 is a pictorial representation of sensors 301 of the wireless earpieces 302 in accordance with illustrative embodiments. As previously noted, the wireless earpieces 302 may include any number of internal or external sensors. As shown the sensors 301 are at least partially external to the wireless earpieces 302 for interacting with the skin, excretions, or tissues of the user. The sensors 301 may make independent measurements or combined measurements utilizing the sensory functionality of each of the sensors to measure, confirm, or verify sensor measurements.

In one embodiment, the sensors 301 may include radar sensors 304, contact sensors 306, and chemical sensors 308. The radar sensors 304 may generate a signal that is communicated to the ear (or other body part) of the user and reflected back. The reflected signal may be analyzed to determine physiological or biometric conditions of the user. For example, the radar sensors may be used to determine pulse rate or other information about the user. Thus, the wireless earpieces 302 may utilize radar sensing as it is known in the art and developing to determine any number of user biometrics.

In one embodiment, the contact sensors 306 may be utilized to perform conductivity, elasticity, and pliability analysis of the user's skin. The contact sensors 306 may measure or provide additional data points and analysis that may indicate the biometric information of the user. The contact sensors 306 may also be utilized to apply electrical, vibrational, motion, or other input, impulses, or signals to the skin of the user.

In another embodiment, one or more lidar sensors 307 may be present to perform imaging. The lidar sensors may be used in a similar manner as opposed to the radar sensors including to detect the same types of biometric information including pulse rate and other minor movements. It is also to be understood that depending, upon what is being measured, the lidar sensors 307 may be otherwise positioned so as to be directed towards the portion of a user where the biometric sensing is to occur.

The chemical sensors 308 may perform chemical analysis of the user's skin, excretions, blood, or any number of internal or external tissues or samples. In one embodiment, the chemical sensors 308 are non-invasive and may only perform chemical measurements and analysis based on the externally measured and detected factors. In other embodiments, one or more probes, vacuums, capillary action components, needles, or other micro-sampling components may be utilized. Minute amounts of blood or fluid may be analyzed to perform chemical analysis that may be reported to the user and others.

The sensors 301 may include parts or components that may be periodically replaced or repaired to ensure accurate measurements.

Figure 4:
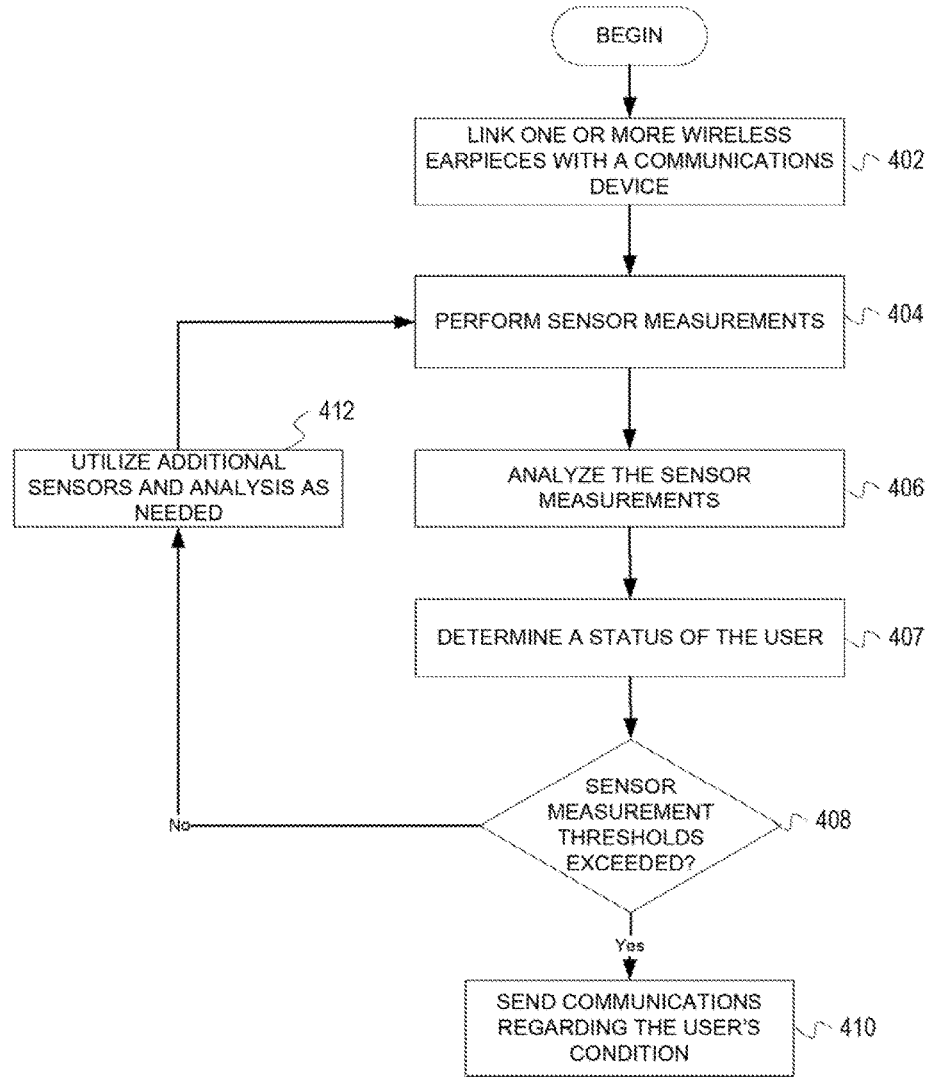
FIG. 4 is a flowchart of a process for determining a condition of a user utilizing wireless earpieces in accordance with an illustrative embodiment.

FIG. 4 is a flowchart of a process for determining a condition of a user utilizing wireless earpieces in accordance with an illustrative embodiment. The process of FIG. 4 may be implemented by one or more wireless earpieces, wearable devices, and any number of other devices communicating directly or through a personal area network. In one embodiment, the process of FIG. 4 may be implemented by one or more wireless earpieces, such as the wireless earpieces 102 of FIG. 1. For example, the method of FIG. 4 may be performed for In one embodiment, the process of FIG. 4 may begin by linking one or more wireless earpieces with a communications device (step 302). The wireless earpieces may be linked with the communications device, such as a smart phone, utilizing any number of communications, standards, or protocols. For example, the wireless earpieces may be linked with a cell phone by a Bluetooth connection. The process may require that the devices be paired utilizing an identifier, such as a passcode, password, serial number, voice identifier, radio frequency, or so forth. The wireless earpieces may be linked with the communications device and any number of other devices directly or through one or more networks, such as a personal area network. In other embodiments, step 402 may not be required to determine the status or condition of a user. For example, any user information may be communicated directly to the user.

Next, the wireless earpieces perform sensor measurements (step 404). The sensor measurements may include performing any number of biometric measurements. In one embodiment, the sensor measurements include at least radar sensor measurements. The measurements may be used to measure pulse. Other biometric sensors, such as optical sensors, mechanical (e.g., vibration, elasticity, tension, etc.) or electrical sensors, may perform additional measurements or confirm or verify the measurements The measurements may also be triggered in response to specific detected events, such as change in user orientation or position (e.g., change from vertical to horizontal position), changes in velocity (e.g., extreme starts, stops, accelerations, etc.), high forces (e.g., impacts, jolts, etc.), or detected events from other sensors worn by the user.

Next, the wireless earpieces analyze the sensor measurements (step 306). The sensor measurements may be processed or otherwise evaluated may the wireless earpieces. For example, one or more processors of the wireless earpieces may process the incoming data measurements from one or more optical, chemical, mechanical, and/or electrical sensors. The sensor measurements are processed for subsequent analysis, determinations, or decisions, implemented by the wireless earpieces.

Next, the wireless earpieces determine a status of the user (step 407). In one embodiment, pulse rate, the detected pigment or chemical levels may be compared against baseline, normative, or threshold levels to determine the status of the user. The sensor measurements may also be compared against previous or historical measurements for the user. The overall physiological status of the user may be utilized or determine to enhance the sensor measurements. For example, sensor measurements corresponding to pulse rate, pulse rate variability, oxygen saturation, temperature, respiratory rate, and systolic and diastolic blood pressure may be utilized as factors, indicators, or other conditions utilized to determine the status of the user. As previously noted, the status or condition of the user may have been previously known or newly determined.

Next, the wireless earpieces determine whether sensor measurement thresholds are exceeded (step 408). The sensor measurement thresholds may also correspond to a specific user status as determined during step 407 and whether that user status is exceeded or not. The wireless earpieces may include any number of thresholds, including, high and low thresholds for measurements and parameters, such as pulse rate, pigment levels or chemical levels. Other sensor thresholds, such as forces experienced by the user, acceleration, temperature, pulse rate, blood oxygenation, blood pressure, user's stated status (e.g., hot, cold, clammy, nauseous, sweaty, faint, etc.) may also be utilized. For example, the wireless earpieces may have a profile that sets two or more thresholds for each biometric reading. In one embodiment, two or more of the thresholds may be violated in order to send communications as specified in step 410 (e.g., ketones, temperature, blood pressure, etc.).

In response to determining the sensor measurement thresholds are exceeded in step 308, the wireless earpieces send communications regarding the user's condition (step 310). In one embodiment, the communications are sent to the communications device linked with the wireless earpieces. The sensor measurements and user's condition may be sent to any number of user's, devices, applications, platforms, or so forth. For example, the communications may be an alert, status update, warning, or other similar information. In one embodiment, the communication may be an alert indicating that one or more biometric measurements has exceeded one or more thresholds (whether high or low). The information from the wireless earpieces may be particularly valuable for users with known medical conditions. The communications device may be monitored by medical professionals, coaches, parents, administrators, caregivers, or any number of other monitoring groups or individuals to ensure the safety of the user.

In response to determining the sensor measurement thresholds are not exceeded in step 408, the wireless earpieces utilize additional sensors and analysis as needed (step 412). In one embodiment, the additional sensors may be worn or integrated with the user. For example, additional measurements may be taken by a smart watch, or chest strap worn by the user. In another example, a pacemaker of the user may provide additional data regarding pulse, heart rhythm, and other applicable or measured information. During step 412, the software utilized by the wireless earpieces or associated wireless devices and control/baseline data utilized to compare the sensor measurements may perform or execute additional analysis, algorithms, processes, or sets of instructions. In one embodiment, additional sensor measurements may be required to definitively determine the status of the user. In one embodiment, the Wireless earpieces may indicate if the status of the user is unknown, undefined, or requires additional analysis during step 408.

Figure 5:
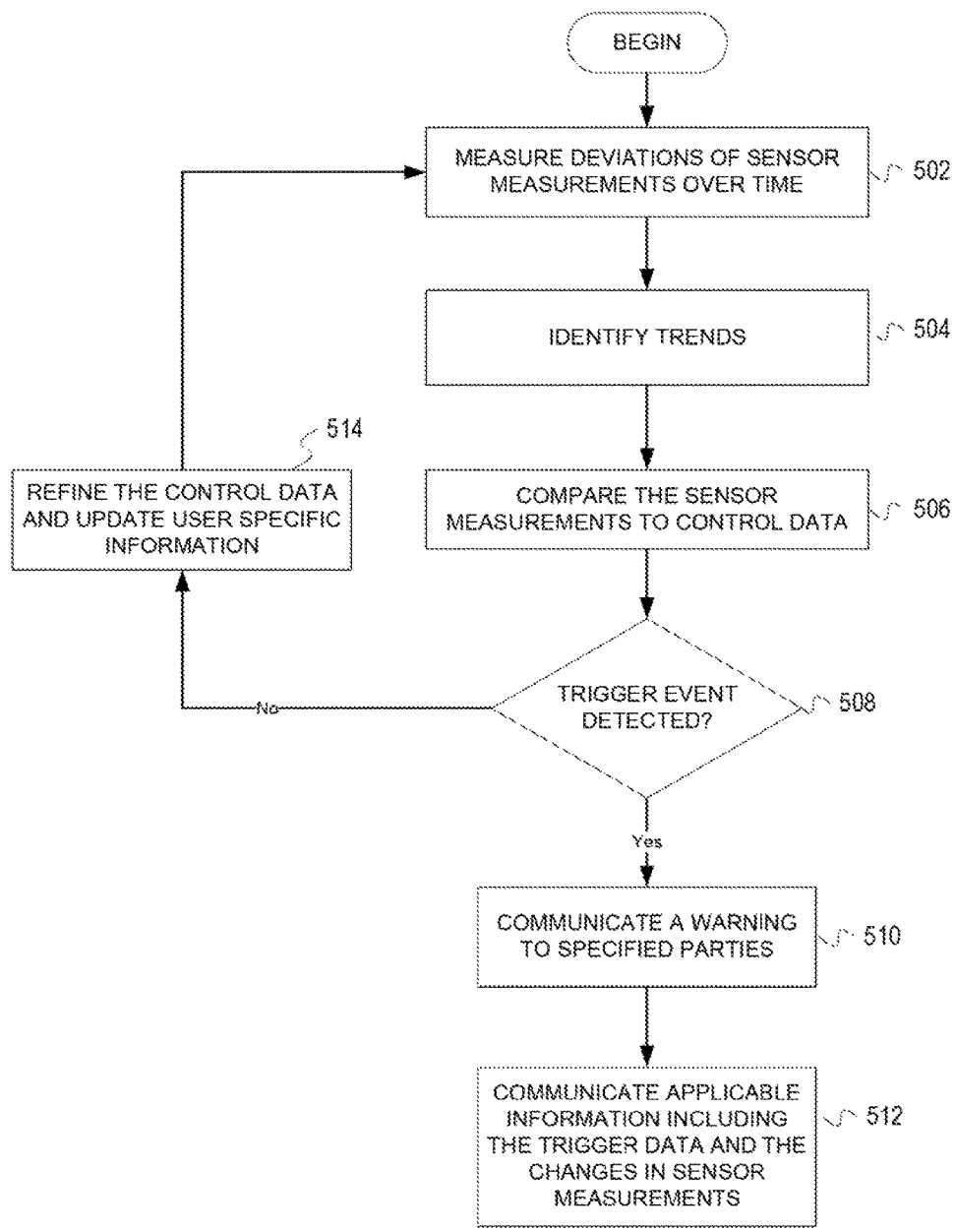
FIG. 5 is a flowchart of a process for monitoring a user utilizing wireless earpieces in accordance with an illustrative embodiment.

FIG. 5 is a flowchart of a process for monitoring a user utilizing wireless earpieces in accordance with an illustrative embodiment. The process of FIG. 5 is similar to that of FIG. 4 and may be performed as part of the process of FIG. 4 or as an independent method or set of steps. The steps of FIG. 4 and FIG. 5 may be integrated or combined in any number of combinations.

The process of FIG. 5 may begin by measuring deviations of sensor measurements over time (step 502). Sensor measurements may be performed constantly, at intervals, or as otherwise specified by the wireless earpieces, the user, or an administrator or other controlling party. As previously noted, the biometric readings taken by the sensors may include ketone levels, pigmentation readings, heart rate, respiratory rate, pulse rate, pulse oximetry, body temperature, systolic and diastolic blood pressure, orientation (e.g., standing, laying down, sitting, etc.), user wakefulness (e.g., sleeping, dreaming, awake, drowsy, etc.), stages of sleep (stages 1, 2, 3, 4, rapid eye movement (REM)), user motion, blood chemical levels, calories burned, sweat levels, and so forth. These sensors may monitor biometrics as well as environmental changes in deviations. For example, the wireless earpieces may note when the user's ketone levels have increased significantly. The wireless earpieces may track multiple biometric and environmental variables over time to best determine the user's condition, activities, mindset, and status.

Next, the wireless earpieces identify trends (step 504), The trend may indicate a general direction, movement, change, or progression of the data measured by the sensors. The trends may be particularly useful for tracking metabolic disorders. In one embodiment, the wireless earpieces may indicate the blood sugar levels of the user to indicate status and generate warnings or alerts. As previously noted, the sensor data may be analyzed by the wireless earpieces alone, by a linked computing or communications device, or utilizing the wireless earpieces at and a combination of other devices, systems, equipment, components, or so forth.

Next, the wireless earpieces compare the sensor measurements to control data (step 506). The control data may correspond to user specific information including baseline readings, default data, or so forth. In one example, the control data may correspond to programmed or baseline data set by the user, such as user biometrics when the user has a normal level of ketones. The control data may also correspond to any number of activities that the user may perform, such as walking, running, swimming, playing sports, sleeping, resting, studying, or any number of activities to ensure that the measurements and user status are accurately determined. For example, there may be natural variations in sensor biometrics based on the activity being performed by the user. The wireless earpieces may also include control data that is determined or aggregated from any number of users. The most appropriate data set may be selected from the control data corresponding to the user's age, sex, ethnicity, weight, or other measured or user entered parameters, factors, and conditions.

Next, the wireless earpieces determine whether a trigger event is detected (step 508). The trigger event may represent any number of thresholds, factors, levels, baseline/comparative readings, or parameters. In one embodiment, the thresholds utilized for the trigger event may include one or more upper or lower threshold levels or values. The determination of step 508 may be made based on the measurements, analysis, and processing performed by the wireless earpieces. In one example, the trigger event may be associated with blood pressure and ketone levels of a user. In another example, the trigger event may be associated with heart rate of the user and blood sugar levels. An event may be triggered in response to 1) the heart rate of the user being above 140 beats per minute (bpm) or below 55 bpm, and/or 2) the blood sugar level of the user exceeding 180. Any combination, group, or sets of one or more, or two or more, or numerous thresholds variables may be set for the thresholds utilized during step 508. In one embodiment, the thresholds may be specified by the user or another party associated with the user based on the user's individual characteristics. In one embodiment, if both the heart rate and blood sugar thresholds are exceeded, the wireless earpieces may trigger a response. In another example, the temperature and blood pressure of the user may also be utilized as factors to determine whether the trigger event is detected.

If the trigger event is reached during step 508, the wireless earpieces communicate a warning to specified parties (step 510). In some embodiments, the warning may represent a health risk to the user. In one example, if biometric readings show a rise in ketones, associated with a concurrent rise in heart rate and respiratory rate, while demonstrating a progressive drop in systolic and diastolic blood pressure, the wireless earpieces may trigger an alert to the user indicating that such patterns are typically associated with a negative metabolic event. As a result, the user may be able to take a break, drink water, visit with a medical professional, or so forth with a similar recommendation communicated to the user as pan of step 510. Any number of devices, users, applications, or other entities may represent the specified parties.

Each of the separate thresholds may be associated with distinct event, alerts or warnings, or indicators presented to the user or specified parties (step 512). As previously noted, the warning may be communicated audibly, tactilely, or electrically (e.g., electrical pulses) through the wireless earpieces. Similarly, the warning may be communicated to any number of other users, systems, administrators, caregivers, medical professionals, or electronic devices directly or through one or more network connections. In one example, the warning may be queued for communication in response to the wireless earpieces being within range of a specified wireless device, interface, network component, or so forth. Even though each threshold, parameter, or value by itself may not be sufficient to trigger the event during step 508, when the thresholds are analyzed together over time, such data may be used to trigger the event so that the user and other specified panics may be warned of potential issues. In some embodiments, the threshold may not be exceeded or passed for the trigger event is reached. For example, if analysis of the sensor measurements and trends show a rate of change for biometric readings that is unacceptable, the trigger event may be reached before the biometric readings even reached the thresholds to best protect the user. The thresholds may also represent rates of change and if those rates of change are exceeded, the trigger event may be detected.

Next, the wireless earpieces communicate applicable information including the trigger data and changes in the sensor measurements (step 512). The applicable information may include the user status (if known), applicable biometric readings, environmental readings corresponding to the user, as well as suggested actions or activities to address the triggered alert. The trigger data and the changes in the sensor measurements are also communicated to the user to give additional background information, details, data, information, and context for why the event was triggered. In one embodiment, the steps 510 and 512 may can be combined into a single step. During steps 510, 512 powerful data analytics are transmitted to the user in an easily understood fashion (e.g., audio alerts, tactile alerts, alerts communicated to an app of a wireless device associated with the wireless earpieces, etc.).

If the trigger event is not reached during step 508, the wireless earpieces refine the control data and update user specific information (step 514). The control data may be updated only as needed to provide the best results and processing of the sensor measurements. During step 514, the wireless earpieces may periodically, intermittently, or as selected by the user update user specific information, such as thresholds utilized to set the trigger events. In one embodiment, the software or algorithms utilized to perform analysis, identification, comparisons, or so forth may be tuned or updated during step 514. Updates may be performed automatically or in response to information and changes from external sources, such as databases, users, systems, or so forth. In some embodiments, no updates, refining, or processing may be performed during step 514. For example, user specific conditions, such as the environment, may be utilized to tune the analysis performed. In hotter environments, the thresholds for the temperature of the user may be increased or decreased accordingly.

Figure 6:
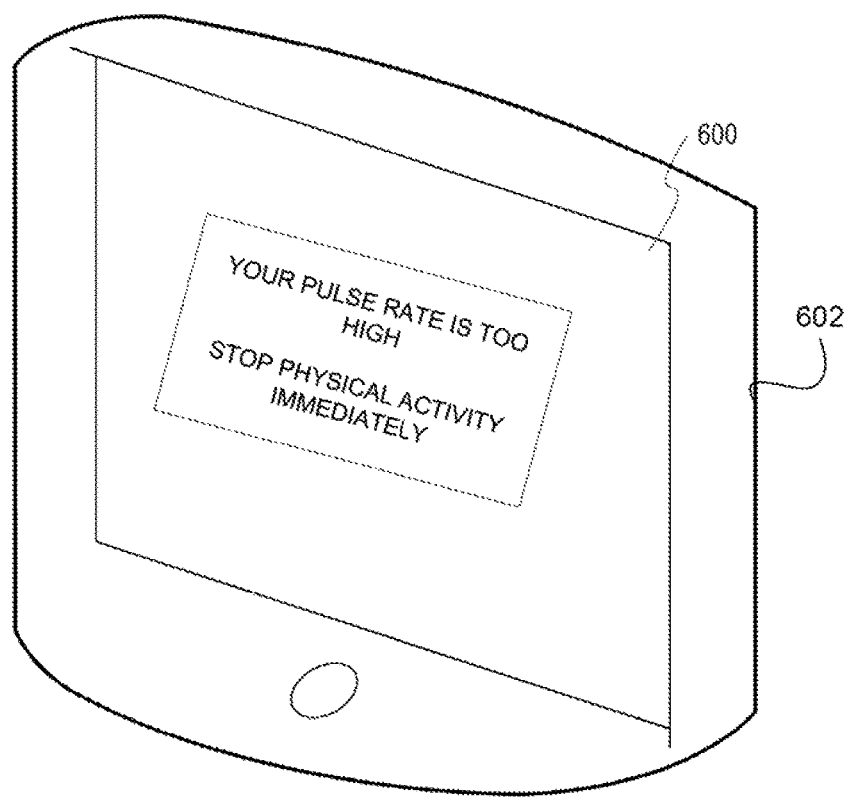
FIG. 6 is a pictorial representation of a display in accordance with an illustrative embodiment.

FIG. 6 is a pictorial representation of a graphical user interface 600 in accordance with an illustrative embodiment. The graphical user interface 600 may be presented by a wireless device 602, such as the wireless device 106 of FIG. 1. In one embodiment, the graphical user interface 600 may present information measured and communicated to the fireless device 602 by the wireless earpieces. The graphical user interface 600 may interact with a user utilizing multivariate parameters, conditions, measurements, and so forth. In one embodiment, the graphical user interface 600 is a display portion of an application utilized to track, communicate, and display user biometrics.

The information presented by the graphical user interface 600 may also be communicated audibly through the wireless earpieces. In addition, any number of communications methods including projection, tactile feedback, and so forth may be used to communicate content captured by the wireless earpieces.

In one embodiment, the graphical user interface 600 may display information, data, and instructions for addressing a user condition determined by user biometrics. For example, the graphical user interface 600 may indicate that the pulse rate of the user is too high or has been too high for a given time period. The graphical user interface 600 may also provide user or condition specific instructions for addressing the user's condition as determined.

In another embodiment, the wireless earpieces may capture information indicating that the user is drinking excessively. Excessive drinking may lead to dangerous conditions, such as alcohol poisoning, drunk driving, passing out, poor decision making, or any number of associated physical or emotional problems. The graphical user interface 600 may provide feedback to the user. The graphical user interface 600 may provide instructions or feedback to the user. For example, the graphical user interface 602 may present a physical or environmental warning. The graphical user interface 600 may also present the biometric readings to the user, such as blood alcohol level, temperature, heart rate, respiration rate, and so forth. The graphical user interface 600 may indicate the user's current biometric readings as well as the threshold that was exceeded to trigger the event, such as the graphical user interface 600 and associated content being displayed to the user or played by the wireless earpieces. The wireless earpieces may also provide feedback to a parent or guardian for an underage user.

The graphical user interface 600 may be utilized to present information as well as receive content from the user. For example, the graphical user interface 600 may receive content from the user including thresholds utilized to generate alerts, authentication settings, alert settings, and so forth. For example, the graphical user interface 600 may indicate that the user should not be driving and may even communicate with one or more vehicle systems to prevent the user from driving.

The illustrative embodiments provide a system, method, personal area network, and wireless earpieces for communicating sensor measurements and an associated user status to a user and one or more externally connected devices. The sensor measurements may be utilized to send communications, updates, alerts, or other information relative to the condition of the user as well as the user's environment. In one embodiment, the sensor measurements may be utilized to protect the user based on one or more sensor measurements that are made, such as potential for disorders, diseases, sicknesses, trauma, or other user conditions. Sensor measurements from other sensors may be utilized to analyze, confirm, or verify the sensor measurements and user condition.

The illustrative embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computing system (or other electronic device(s)) to perform a process according to embodiments, whether presently described or not, since every conceivable variation is not enumerated herein. A machine readable medium includes any mechanism for storing or transmitting information in a form (e.g., software, processing application) readable by a machine (e.g., a computer). The machine-readable medium may include, but is not limited to, magnetic storage medium); optical storage medium; magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications medium.

Computer program code for carrying out operations of the embodiments may be written in any combination of one or more programming languages, including an object oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection maybe made to an external computer (e.g., through the Internet using an Internet Service Provider).

Figure 7:
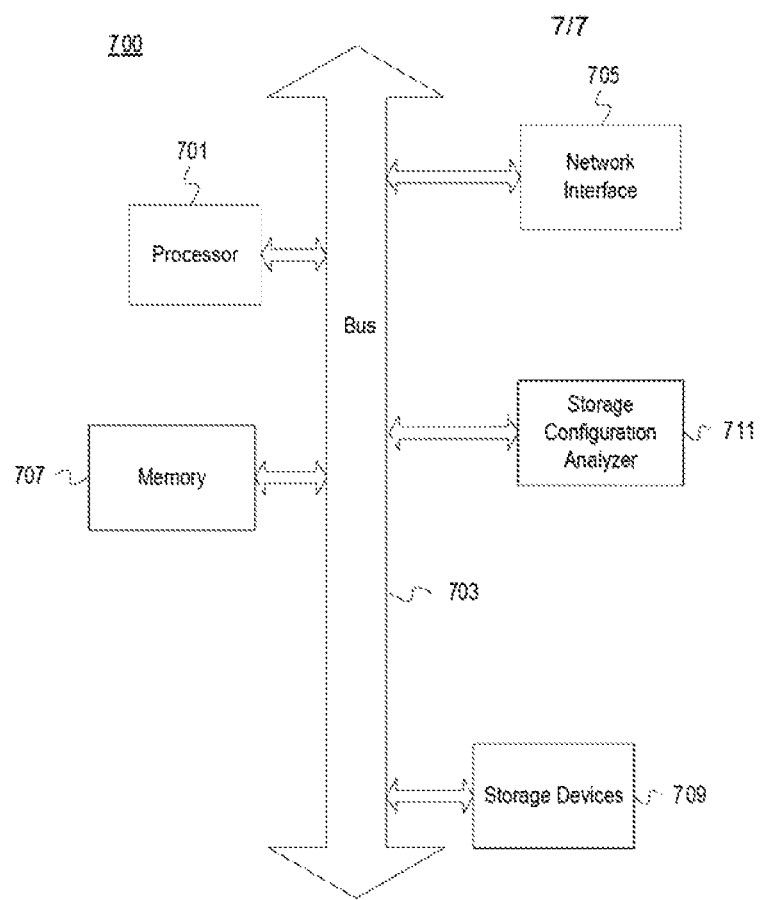
FIG. 7 depicts a computing system in accordance with an illustrative embodiment.

FIG. 7 depicts a computing system 700 in accordance with an illustrative embodiment. For example, the computing system 700 may represent a device, such as the wireless device 204 of FIG. 2. The computing system 700 includes a processor unit 701 (possibly including multiple processors, multiple cores, multiple nodes, and/or implementing multi-threading, etc.). The computing system includes memory 707. The memory 707 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 703 (e.g., PCI, ISA, PCI-Express, HyperTransport®, InfiniBand®, NuBus, etc.), a network interface 706 (e.g., an ATM interface, an Ethernet interface, a Frame Relay interface, SONET interface, wireless interface, etc.), and a storage device(s) 709 (e.g., optical storage, magnetic storage, etc.). The system memory 707 embodies functionality to implement embodiments described above. The system memory 707 may include one or more functionalities that facilitate retrieval of the audio information associated with an identifier. Code may be implemented in any of the other devices of the computing system 700. Any one of these functionalities may be partially (or entirely) implemented in hardware and/or on the processing unit 701. For example, the functionality may be implemented with an application specific integrated circuit, in logic implemented in the processing unit 701, in a co-processor on a peripheral device or card, etc. Further, realizations may include fewer or additional components not illustrated in FIG. 7 (e.g., video cards, audio cards, additional network interfaces, peripheral devices, etc.). The processor unit 701, the storage device(s) 709, and the network interface 705 are coupled to the bus 703. Although illustrated as being coupled to the bus 703, the memory 707 may be coupled to the processor unit 701.

The features, steps, and components of the illustrative embodiments may be combined in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A method for determining a status of a user utilizing wireless earpieces, comprising:
    performing sensor measurements of a user utilizing at least a radar sensor of the wireless earpieces, wherein the radar sensor is oriented to detect movement of a tympanic membrane of the user while the user is wearing the wireless earpieces;
    wherein the performing sensor measurements is triggered in response to a change in user orientation of the user;
    analyzing the sensor measurements; and
    determining the status of the user utilizing at least sensor measurements from the radar sensor of the wireless earpieces.

2. The method of claim 1, wherein the analyzing comprises:
    measuring deviations of the sensor measurements over time, identifying trends associated with the sensor measurements, and comparing the sensor measurements to control data for the user.

3. The method of claim 1 wherein the sensor measurements further include lidar measurements from a lidar sensor.

4. A wireless earpiece comprising:
    a processor for executing a set of instructions; and
    a memory for storing the set of instructions, wherein the set of instructions are executed to:
    perform sensor measurements of a user utilizing a radar sensor of the wireless earpiece, wherein the radar sensor is integrated with the processor and oriented to detect movement of a tympanic membrane of the user while the user is wearing the wireless earpiece;
    wherein the performance of the sensor measurements are triggered in response to a change in user orientation of the user;
    analyze the sensor measurements; and
    determine the status of the user utilizing at least sensor measurements from the radar sensor of the wireless earpiece.

5. The wireless earpieces of claim 4, wherein the set of instructions are further executed to:
    analyze the sensor measurements by measuring deviations over time,
    identify trends associated with the sensor measurements, and
    compare the sensor measurements to control data for the user.

6. A method for determining a status of a user utilizing wireless earpieces, comprising:
    performing sensor measurements of a user utilizing at least a radar sensor of the wireless earpieces, wherein the radar sensor is oriented to detect movement of a tympanic membrane of the user while the user is wearing the wireless earpieces;
    wherein the radar sensor is configured to map a topography of the tympanic membrane of the user;
    analyzing the sensor measurements, wherein the topography of the tympanic membrane Is used to identify the user; and
    determining the status of the user utilizing at least sensor measurements from the radar sensor of the wireless earpieces.

7. The method of claim 6, wherein the topography is a three-dimensional topography.

* * * * *